United States Patent [19]

Maienfisch et al.

[11] Patent Number: 5,245,040

[45] Date of Patent: Sep. 14, 1993

[54] PROCESS FOR THE PREPARATION OF NITROGUANIDINE DERIVATIVES

[75] Inventors: Peter Maienfisch, Rodersdorf; Odd Kristiansen, Möhlin; Laurenz Gsell, Basel, all of Switzerland

[73] Assignee: Ciba-Geigy Corporation, Ardsley, N.Y.

[21] Appl. No.: 777,856

[22] Filed: Oct. 16, 1991

[30] Foreign Application Priority Data

Oct. 24, 1990 [CH] Switzerland ................. 3395/90

[51] Int. Cl.$^5$ ................. C07D 213/02; C07D 277/20; C07D 279/06; C07D 279/12
[52] U.S. Cl. ........................... 546/332; 544/8; 544/53; 544/54; 544/58.2; 544/58.4; 544/67; 544/68; 544/96; 544/97; 544/98; 544/182; 544/194; 544/212; 544/224; 544/298; 544/238; 544/239; 544/240; 544/241; 544/316; 544/322; 544/333; 544/334; 544/335; 544/336; 546/114; 546/118; 546/125; 546/275; 546/280; 546/284; 546/286; 546/288; 546/290; 546/296; 546/300; 546/301; 546/302; 546/304; 546/312; 546/338; 548/127; 548/128; 548/134; 548/136; 548/143; 548/146; 548/182; 548/183; 548/184; 548/186; 548/189; 548/190; 548/191; 548/193; 548/214; 548/233; 548/240; 548/243; 548/244; 548/245; 548/247; 548/250; 548/254; 548/262.8; 548/263.4; 548/303.1; 548/336.1; 548/323.5; 548/375.1; 548/541; 548/561; 549/61; 549/62; 549/75; 549/474; 549/475; 549/480; 549/491
[58] Field of Search ............. 546/275, 280, 286, 287, 546/288, 289, 297, 300, 302, 329, 345, 114, 118, 125, 284, 290, 296, 301, 304, 312, 332, 338; 544/194, 212, 8, 53, 54, 58.2, 58.4, 67, 68, 96, 97, 98, 182, 194, 212, 224, 298, 238, 239, 240, 241, 316, 322, 333, 334, 335, 336; 548/252, 254, 255, 262.8, 263.2, 263.4, 324, 335, 127, 128, 134, 336, 337, 136, 143, 146, 341, 182, 183, 184, 356, 186, 189, 190, 191, 193, 214, 225, 226, 240, 243, 233, 235, 240, 243, 244, 245, 247, 250, 251; 549/61, 62, 75, 474, 475, 480, 491

[56] References Cited

U.S. PATENT DOCUMENTS 4,937,340  6/1990  Huang ........................ 544/194

FOREIGN PATENT DOCUMENTS

| 0375907 | 7/1990 | European Pat. Off. . |
| 0376279 | 7/1990 | European Pat. Off. . |
| 0383091 | 8/1990 | European Pat. Off. . |
| 0386565 | 9/1990 | European Pat. Off. . |
| 0428941 | 5/1991 | European Pat. Off. . |
| 0483055 | 4/1992 | European Pat. Off. . |
| 9101978 | 2/1991 | Japan . |

OTHER PUBLICATIONS

Derwent Abstract 92-045988/06 of the Japanese 3291-267-A, 1990.

Primary Examiner—Mukund J. Shah
Assistant Examiner—Y. N. Gupta
Attorney, Agent, or Firm—Kevin T. Mansfield; Edward McC. Roberts

[57] ABSTRACT

A process for the preparation of 1,3-disubstituted 2-nitroguanidines of the formula I

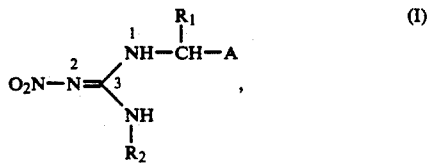

in which $R_1$ is hydrogen or $C_1$–$C_4$alkyl, $R_2$ is hydrogen, $C_1$–$C_6$alkyl, $C_3$–$C_6$cycloalkyl or a radical —$CH_2B$; A is an unsubstituted or mono- to tetrasubstituted aromatic or non-aromatic, monocyclic or bicyclic heterocyclic radical, which may contain one or two substituents from the group comprising $C_1$–$C_3$haloalkyl having 1 to 7 halogen atoms, cyclopropyl, halocyclopropyl having 1 to 3 halogen atoms, $C_2$–$C_3$alkenyl, $C_2$–$C_3$alkynyl, $C_2$–$C_3$haloalkenyl and $C_2$–$C_3$haloalkynyl having 1 to 4 halogen atoms, $C_1$–$C_3$haloalkoxy having 1 to 7 halogen atoms, $C_1$–$C_3$alkylthio, $C_1$–$C_3$haloalkylthio having 1 to 7 halogen atoms, allyloxy, propargyloxy, allylthio, pro- (Abstract continued on next page.)

pargylthio, haloallyloxy, haloallylthio, cyano and nitro and one to four substituents from the group comprising $C_1$–$C_3$alkyl, $C_1$–$C_3$alkoxy and halogen; and B is optionally substituted phenyl or pyridyl, which comprises hydrolysing a compound of the formula II

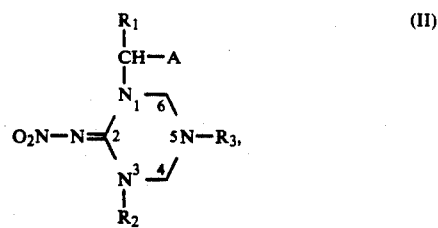

in which $R_3$ is unsubstituted or substituted $C_1$–$C_{10}$alkyl, $C_3$–$C_6$cycloalkyl, phenyl or benzyl.

The compounds of the formula I are suitable as intermediates for the preparation of pesticides.

16 Claims, No Drawings

PROCESS FOR THE PREPARATION OF NITROGUANIDINE DERIVATIVES

The present invention relates to a novel process for the preparation of substituted 2-nitroguanidine derivatives.

It has already been disclosed that, for the preparation of 1,3-disubstituted 2-nitroguanidines, a further substituent can be introduced (for example by alkylation) into monosubstituted 2-nitroguanidines (cf. for example EP Patent Applications 0.375.907, 0.376.279 and 0.383.091). Owing to the presence of three reactive hydrogen atoms in the monosubstituted 2-nitroguanidines used as starting material in these reactions, the substitution reactions of this type proposed hitherto often proceed unselectively and lead to undesired substitution products. In the EP patent applications mentioned, the preparation of 1,3-disubstituted 2-nitroguanidines is described by reaction of monosubstituted nitroisothioureas with primary amines with elimination of mercaptan. However, these nitroisothiourea compounds containing alkylthio leaving groups and proposed as starting compounds in the said known processes are only accessible with difficulty.

The aim of the present invention is an improved process for the preparation of 1-monosubstituted and 1,3-disubstituted 2-nitroguanidines from easily obtainable starting compounds, which permits 1,3-disubstitution in a controlled manner without formation of relatively large amounts of undesired by-products.

According to the invention, a process for the preparation of 1,3-disubstituted and also 1-monosubstituted 2-nitroguanidines of the formula I

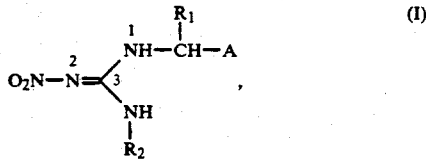

is now proposed in which $R_1$ is hydrogen or $C_1$-$C_4$alkyl, $R_2$ is hydrogen, $C_1$-$C_6$alkyl, $C_3$-$C_6$cycloalkyl or a radical —$CH_2B$; A is an unsubstituted or mono- to tetrasubstituted aromatic or non-aromatic, monocyclic or bicyclic heterocyclic radical, which may contain one or two substituents from the group comprising $C_1$-$C_3$haloalkyl having 1 to 7 halogen atoms, cyclopropyl, halocyclopropyl having 1 to 3 halogen atoms, $C_2$-$C_3$alkenyl, $C_2$-$C_3$alkynyl, $C_2$-$C_3$haloalkenyl and $C_2$-$C_3$haloalkynyl having 1 to 4 halogen atoms, $C_1$-$C_3$haloalkoxy having 1 to 7 halogen atoms, $C_1$-$C_3$haloalkylthio having 1 to 7 halogen atoms, allyloxy, propargyloxy, allylthio, propargylthio, haloallyloxy, haloallylthio, cyano and nitro and one to four substituents from the group comprising $C_1$-$C_3$alkyl, $C_1$-$C_3$alkoxy and halogen; and B is phenyl, cyanophenyl, nitrophenyl, halophenyl having 1 to 3 halogen atoms, phenyl substituted by $C_1$-$C_3$alkyl, $C_1$-$C_3$haloalkyl having 1 to 7 halogen atoms, $C_1$-$C_3$alkoxy or $C_1$-$C_3$haloalkoxy having 1 to 7 halogen atoms, 3-pyridyl, 5-thiazolyl, 5-thiazolyl substituted by one or two substituents from the group comprising $C_1$-$C_3$alkyl, $C_1$-$C_3$haloalkyl having 1 to 7 halogen atoms, cyclopropyl, halocyclopropyl, $C_2$-$C_3$alkenyl, $C_2$-$C_3$alkynyl, $C_1$-$C_3$alkoxy, $C_2$-$C_3$haloalkenyl and $C_2$-$C_3$haloalkynyl having 1 to 4 halogen atoms, $C_1$-$C_3$haloalkoxy having 1 to 7 halogen atoms, $C_1$-$C_3$alkylthio, $C_1$-$C_3$haloalkylthio having 1 to 7 halogen atoms, allyloxy, propargyloxy, allylthio, propargylthio, haloallyloxy, haloallylthio, halogen, cyano and nitro, or 3-pyridyl substituted by one or two radicals from the group comprising $C_1$-$C_3$haloalkyl having 1 to 7 halogen atoms, cyclopropyl, halocyclopropyl, $C_2$-$C_3$alkenyl, $C_2$-$C_3$alkynyl, $C_2$-$C_3$haloalkenyl and $C_2$-$C_3$haloalkynyl having 1 to 4 halogen atoms, $C_1$-$C_3$haloalkoxy having 1 to 7 halogen atoms, $C_1$-$C_3$alkylthio, $C_1$-$C_3$haloalkylthio having 1 to 7 halogen atoms, allyloxy, propargyloxy, allylthio, propargylthio, haloallyloxy, haloallylthio, cyano and nitro or by one to four radicals from the group comprising $C_1$-$C_3$alkyl, $C_1$-$C_3$alkoxy and halogen, which comprises hydrolysing a compound of the formula II

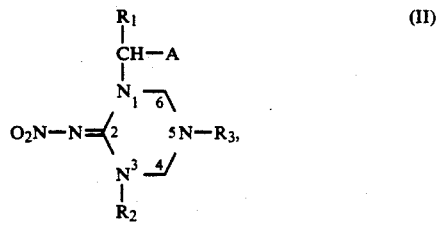

in which $R_3$ is unsubstituted or substituted $C_1$-$C_{10}$alkyl, $C_3$-$C_6$cycloalkyl, phenyl or benzyl.

The substituted 2-nitroguanidines prepared according to the invention can also occur as double bone isomers with respect to the —N=C(2) bond and in their tautomeric forms (formulae I, Ia, Ib):

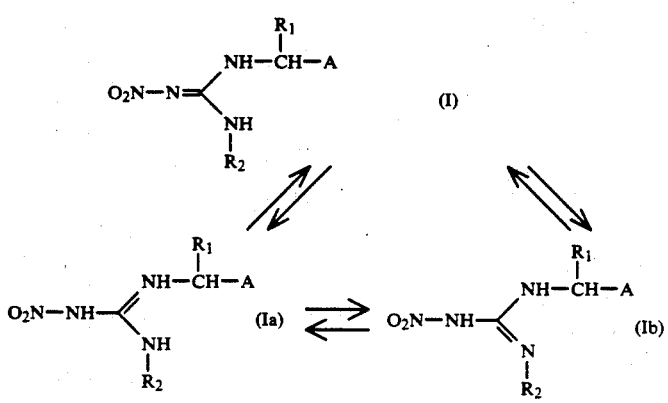

Formula I according to the invention is accordingly to be understood in the sense that the corresponding double bond isomers and the structures as in the formulae Ia and Ib are also included in the manner of writing formula I.

In the definition of the above formulae I and II, the individual generic terms should be understood as follows:

The halogen atoms possible as substituents are both fluorine and chlorine and also bromine and iodine, fluorine, chlorine and bromine being preferred. Halogen in this case is to be understood as an independent substituent or as part of a substituent, such as in haloalkyl, haloalkylthio, haloalkoxy, halocycloalkyl, haloalkenyl, haloalkynyl, haloallyloxy or haloallylthio. The alkyl, alkylthio, alkenyl, alkynyl and alkoxy radicals possible as substituents can be straight-chain or branched. Examples of alkyls of this type are methyl, ethyl, propyl, isopropyl, butyl, i-butyl, sec-butyl or tert-butyl. Suitable alkoxy radicals, inter alia, are: methoxy, ethoxy, propoxy, isopropoxy or butoxy and their isomers. Alkylthio, for example, is methylthio, ethylthio, isopropylthio, propylthio or the isomeric butylthios. If the alkyl, alkoxy, alkenyl, alkynyl or cycloalkyl groups possible as substituents are substituted by halogen, they may be only partially halogenated or alternatively perhalogenated. The definitions given above apply in this case to halogen, alkyl and alkoxy. Examples of the alkyl elements of these groups are methyl mono- to trisubstituted by fluorine, chlorine and/or bromine, for example $CHF_2$ or $CF_3$, ethyl mono-to pentasubstituted by fluorine, chlorine and/or bromine, for example $CH_2CF_3$, $CF_2CF_2$, $CF_2CCl_3$, $CF_2CHCl_2$, $CF_2CHF_2$, $CF_2CFCl_2$, $CF_2CHBr_2$, $CF_2CHClF$, $CF_2CHBrF$ or $CClFCHClF$, propyl or isopropyl mono- to heptasubstituted by fluorine, chlorine and/or bromine, for example $CH_2CHBrCH_2Br$, $CF_2CHFCF_3$, $CH_2CF_2CF_3$ or $CH(CF_3)_2$, butyl mono- to nonasubstituted by fluorine, chlorine and/or bromine or one of its isomers, for example $CF(CF_3)CHFCF_3$ or $CH_2(CF_2)_2CF_3$, 2-chlorocyclopropyl or 2,2-difluorocyclopropyl, 2,2-difluorovinyl, 2,2-dichlorovinyl, 2-chloroalkyl, 2,3-dichlorovinyl or 2,3-dibromovinyl.

If the alkyl, alkoxy or cycloalkyl groups defined are substituted by other substituents, they may be mono- or polysubstituted by the same or different types of the substituents enumerated. Preferably, one or two further substituents are present in the substituted groups. The cycloalkyl radicals possible as substituents are, for example, cyclopropyl, cyclobutyl, cyclopentyl or cyclohexyl. Alkenyl and alkynyl groups contain an unsaturated carbon-carbon bond. Typical representatives are allyl, methallyl or propargyl, but also vinyl and ethynyl. The double or triple bonds in allyloxy, propargyloxy, allylthio or propargylthio are preferably separated from the linkage site to the hetero atom (O or S) by a saturated carbon atom.

The hydrolysis process according to the invention is preferably carried out as an acidic hydrolysis at normal pressure and at a temperature from 0° to 120° C., preferably 20° to 80° C., in a solvent or diluent which is inert to the reaction components. Preferably, a compound of the formula II is hydrolysed in an aqueous-acidic medium, it being possible to use mineral acids, such as HCl or $H_2SO_4$ and organic acids, such as alkylcarboxylic acids and sulfonic acids, as the acid. Suitable solvents are particularly alcohols, such as methanol, ethanol and propanol, and especially water. Further suitable solvents are, for example, ethers, such as tetrahydrofuran and dioxane, and also other solvents which do not impair the reaction. The solvents can also be used as mixtures.

In formula II, suitable substituents for the radical $R_3$ can be alkyl, cycloalkyl, phenyl or benzyl groups, halogen or one or more optionally organic radicals, which are preferably bonded to the alkyl, cycloalkyl, phenyl or benzyl groups via a C, O or S atom.

To carry out the process according to the invention, those compounds of the formula II are preferably used as starting materials in which $R_3$ is $C_1$–$C_{10}$alkyl, $C_3$–$C_6$cycloalkyl, $C_1$–$C_{10}$alkyl, substituted by 1–12 radicals from the group comprising halogen, hydroxyl, $C_1$–$C_4$alkoxy, $C_1$–$C_4$haloalkoxy having 1 to 9 halogen atoms, di($C_1$–$C_4$alkyl)amino and $C_1$–$C_5$alkoxycarbonyl, $C_3$–$C_6$cycloalkyl substituted by 1–4 $C_1$–$C_4$alkyl radicals or halogen atoms, phenyl, benzyl, or phenyl or benzyl substituted by 1–3 ring substituents from the group comprising halogen, $C_1$–$C_4$alkyl, $C_1$–$C_4$haloalkyl having 1 to 9 halogen atoms, $C_1$–$C_4$alkoxy, $C_1$–$C_4$haloalkoxy having 1 to 9 halogen atoms, $C_1$–$C_4$alkylthio, nitro and cyano.

The process according to the invention is especially used for the preparation of compounds of the formula I in which the heterocyclic radical A is preferably unsaturated and is bonded to the parent substance of the formula I via a carbon atom as the ring member. In particular, examples of heterocycles of the definition A according to the invention are found in the parent groups of the following structures:

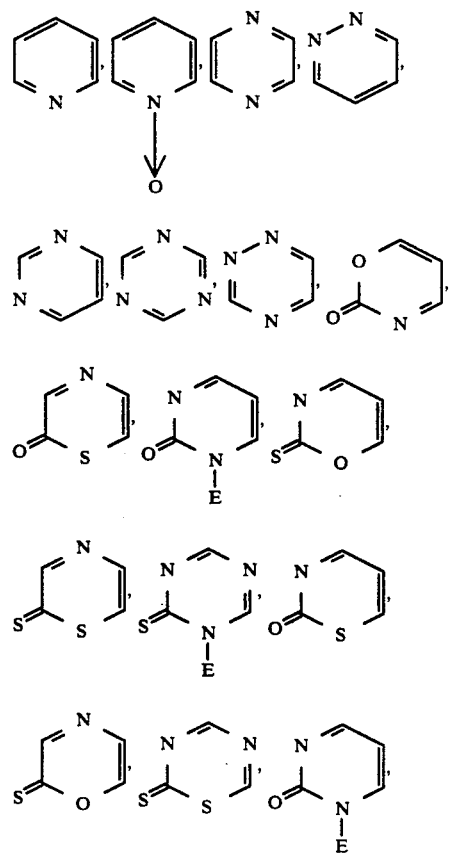

-continued
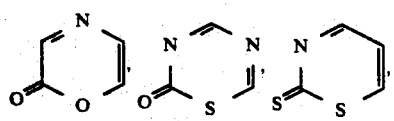
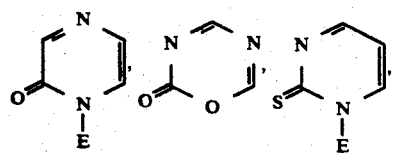
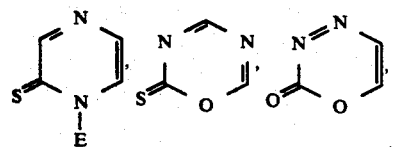
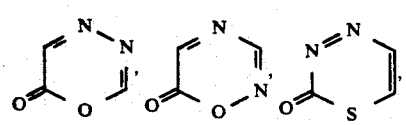
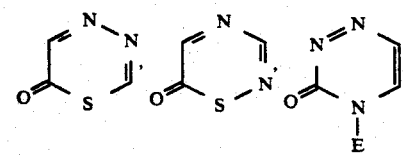
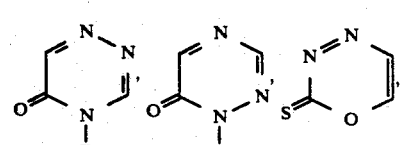
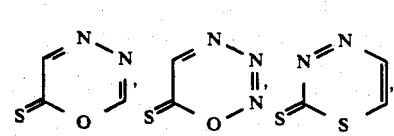
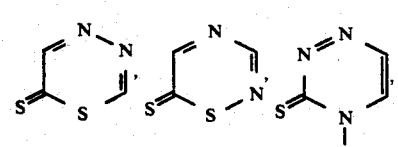
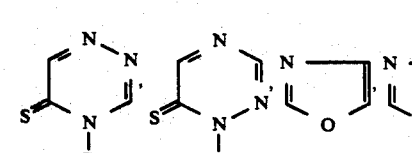
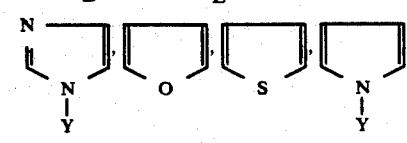
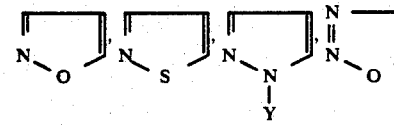
-continued
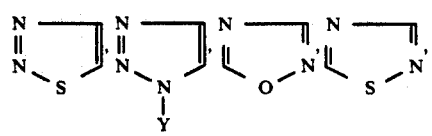
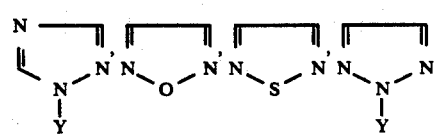
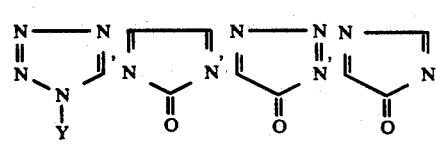
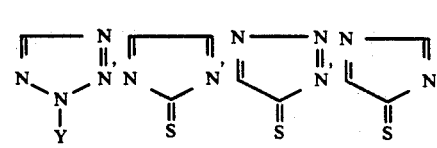
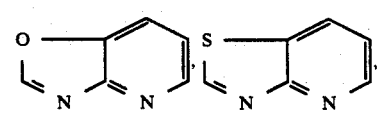
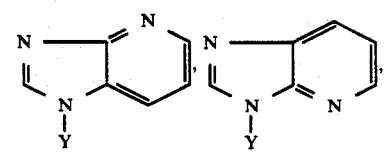
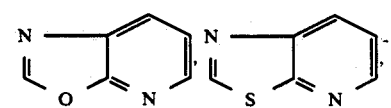
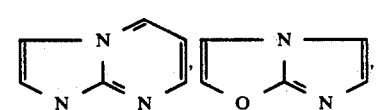
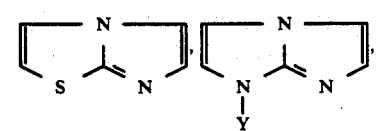
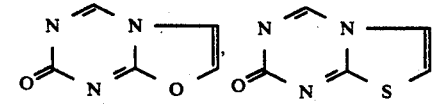
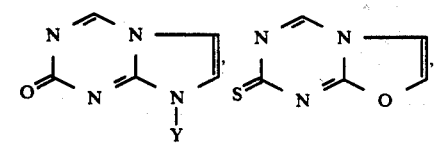

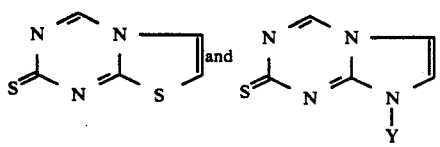

In the above formulae E is $C_1-C_3$alkyl and Y is hydrogen, $C_1-C_3$alkyl or cyclopropyl.

The heterocycles A enumerated above as examples can be unsubstituted or, depending on the substitution possibilities of the ring system, carry up to four substituents, such as are given under formula I. Preferably, these heterocycles carry one to three substituents from the group comprising halogen, $C_1-C_3$alkyl, $C_1-C_3$-haloalkyl and $C_1-C_3$haloalkoxy each having 1 to 7 halogen atoms, and $C_1-C_3$alkoxy. Particularly preferred heterocycles A are pyridyl radicals or thiazolyl radicals, for example 3-pyridyl, 2-halopyrid-5-yl, 2,3-dihalopyrid-5-yl, 2-halothiazol-4-yl, 1-oxopyrid-3-yl, 1-oxo-2-halopyrid-5-yl and 1-oxo-2,3-dihalopyrid-5-yl.

Furthermore, compounds of the formula I according to the invention are preferably prepared in which the radical B is a phenyl, 3-pyridyl or 5-thiazolyl radical, which can be unsubstituted or substituted by one or two radicals from the group comprising halogen, $C_1-C_3$alkyl, $C_1-C_3$haloalkyl and $C_1-C_3$haloalkoxy each having 1 to 7 halogen atoms and, $C_1-C_3$alkoxy.

Among the compounds of the formula I to be prepared according to the invention, those are to be emphasised in which $R_1$ is hydrogen, $R_2$ is hydrogen, methyl, ethyl or cyclopropyl and A is pyridyl, 1-oxopyridyl, thiazolyl or pyridyl, 1-oxopyridyl or thiazolyl which are each substituted by one to three substituents from the group comprising halogen, $C_1-C_3$alkyl, $C_1-C_3$haloalkyl and also $C_1-C_3$haloalkoxy having 1 to 7 halogen atoms and $C_1-C_3$alkoxy. In this sense, the preparation of those compounds of the formula I is also of interest in which a) $R_1$ is hydrogen, and/or
b) $R_2$ is hydrogen, $C_1-C_3$alkyl or cyclopropyl, and/or
c) A is 2-chloropyrid-5-yl or 2-chlorothiazol-5-yl.

Of particular biological interest are compounds of the formula I in which $R_2$ is methyl.

The compounds of the formula I prepared according to the invention are useful active substances for pest control and have favourable tolerability to warm-blooded animals, fish and plants. In particular, the compounds of the formula I are suitable for controlling insects and arachnida which occur in crop plants and ornamentals in agriculture, in particular in crops of cotton, vegetables and fruits, in forestry, in the storage and protection of materials and in the hygiene sector, in particular in household animals and productive livestock. The compounds are especially effective against sucking insects which are harmful to plants, in particular against aphids and siccadas. Substituted 2-nitroguanidines of the type which can be prepared according to the invention having pesticidal activity are described, for example, in EP Patent Applications 376.279, 375.907 and 383.091.

The possible starting compounds or intermediates of the formulae II and V for the process according to the invention are novel 2-nitroimino-1,3,5-triazacyclohexane derivatives. The processes described for the preparation of the intermediates of the formulae II and V are also a part of the invention.

The compounds of the formula II can be obtained by
a) reacting a compound of the formula III

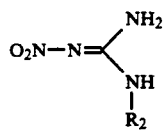
(III)

with formaldehyde, or paraformaldehyde, and a compound of the formula IV $$H_2N-R_3 \quad (IV)$$

and
b) reacting the resulting compound of the formula V

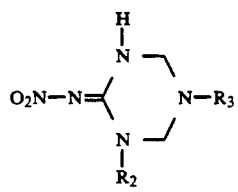
(V)

with a compound of the formula VI $$\underset{\underset{CH}{|}}{X}-\underset{|}{CH}-A \quad (VI)$$

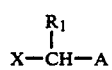

whereby in the formulae II to VI the radicals $R_1$, $R_2$, $R_3$ and A have the meanings given above and X is a leaving group.

Examples of possible leaving groups X in the context of the procedure described are: halogen, preferably chlorine, bromine or iodine, or sulfonic acid radicals, such as alkylsulfonic acid radicals, mesylate or tosylate.

Step a) of the above process for the preparation of the compounds of the formula II is advantageously carried out at normal pressure, if appropriate also at elevated pressure in an inert solvent and at temperatures between 0° C. and +140° C., preferably between +20° C. and +120° C. Suitable solvents are particularly alcohols, such as methanol, ethanol and propanol, as well as water. Other suitable solvents are, for example, aromatic hydrocarbons, such as benzene, toluene and xylene, ethers such as tetrahydrofuran, dioxane and diethyl ether, halogenated hydrocarbon, such as methylene chloride, chloroform, carbon tetrachloride and chlorobenzene and other solvents which do not impair the reaction. The solvents can also be used as mixtures. If appropriate, the reaction is carried out with the addition of an acid catalyst, such as HCl, $H_2SO_4$ or a sulfonic acid, such as p-toluenesulfonic acid. The water of reaction formed can optionally be removed by means of a water separator or by addition of molecular sieve. The abovementioned process step b) can preferably be carried out at normal or slightly elevated pressure and in the presence of preferably aprotic solvents or diluents. Suitable solvents or diluents are, for example, ethers and ether-like compounds, such as diethyl ether, dipropyl ether, dibutyl ether, dioxane, dimethoxy ethers and tetrahydrofuran, aliphatic, aromatic and halogenated hydrocarbons, in particular benzene, toluene, xylene, chloroform, methylene chloride, carbon tetrachloride and chlorobenzene, nitriles, such as acetonitrile or propionitrile, dimethyl sulfoxide or dimethylformamide and also mixtures of these solvents. This process step is in general carried out at a temperature of −20° to +140° C., preferably between 0° and +120° C., preferably in the presence of a base. Suitable bases are, for example, carbonates, such as sodium carbonate and potassium carbonate. Hydrides, such as sodium hydride, potassium hydride and calcium hydride, can also be employed as bases. The reaction may optionally also be carried out in the presence of a catalyst, for example caesium chloride.

The starting products of the above formulae IV and VI are known and commercially available or can be prepared easily in analogy to known processes. The 2-nitroguanidine starting products of the formula III are also known; they can advantageously be prepared from S-methyl-N-nitroisothiourea by reaction with an appropriate primary amine (cf. U.S. Pat. Nos. 4,804,780 and 4,221,802). S-Methyl-N-nitroisothiourea is obtained in good yield by nitration of S-methylisothiourea [cf. J. Am. Chem. Soc. 76, 1877 (1954)].

EXAMPLE 1

Preparation of the intermediates of the formula V a) Preparation of 2-nitroimino-5-methyl-1,3,5-triazacyclohexane:

A mixture of 26.0 g of nitroguanidine, 31.1 ml of an 8M solution of methylamine in ethanol, 38 ml of a 37% solution of formaldehyde in water and 100 ml of ethanol is heated at 50° C. for 2 hours and then filtered. The crystals obtained are washed three times with 20 ml portions of ethanol and then dried. 25.2 g of the title compound, m.p. 173°–175° C., of the formula

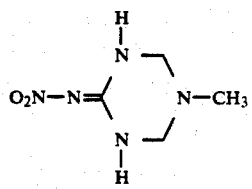

(Compound No. 3.01)

are obtained.

b) Preparation of 1-methyl-2-nitroimino-5-n-propyl-1,3,5-triazacyclohexane:

A mixture of 17.1 g of 1-methyl-2-nitroguanidine, 12.0 ml of n-propylamine, 22.0 ml of a 37% solution of formaldehyde in water and 40 ml of ethanol is heated at 50° C. for 4 hours. A further 7.0 ml of n-propylamine and 13 ml of a 37% solution of formaldehyde in water are then added. After stirring at 50° C. for 2 hours, the reaction mixture is evaporated in vacuo and the precipitated crystals are stirred with ether. 26.9 g of the title compound, m.p. 84°–86° C., of the formula

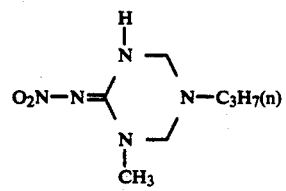

(Compound No. 3.11)

are obtained.

c) Preparation of 1-methyl-2-nitroimino-5-phenyl-1,3,5-triazacyclohexane:

A mixture of 2.36 g of 1-methyl-2-nitroguanidine, 2.11 ml of aniline, and 1.80 g of paraformaldehyde in 30 ml of toluene is treated with 3 drops of concentrated HCl solution and then boiled for 6 hours in a water separator. The reaction mixture is then evaporated in vacuo and the crude product obtained as the residue is recrystallised from methanol. The title compound, m.p. 169°–172° C., of the formula

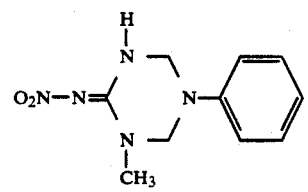

(Compound No. 3.38)

is obtained.

The following compounds of the formula V shown in Table I are obtainable analogously to the working methods described above:

TABLE I

| Compd. No. | $R_2$ | $R_3$ | Physical data |
|---|---|---|---|
| 3.01 | H | —CH$_3$ | m.p. 173–175° C. |
| 3.02 | H | —C$_2$H$_5$ | m.p. 181–182° C. |
| 3.03 | H | —C$_3$H$_7$(n) | |
| 3.04 | H | —CH(CH$_3$)$_2$ | |
| 3.05 | H | ◁ | m.p. 225–227° C. |
| 3.06 | H | ⬡H | |
| 3.07 | H | ⬡ | |

TABLE I-continued

| Compd. No. | R₂ | R₃ | Physical data |
|---|---|---|---|
| 3.08 | H | —CH₂—C₆H₅ | |
| 3.09 | —CH₃ | —CH₃ | m.p. 134–135° C. |
| 3.10 | —CH₃ | —C₂H₅ | m.p. 112–113° C. |
| 3.11 | —CH₃ | —C₃H₇(n) | m.p. 84–86° C. |
| 3.12 | —C₂H₅ | —CH₃ | |
| 3.13 | —C₂H₅ | —C₂H₅ | m.p. 95–96° C. |
| 3.14 | —C₂H₅ | —C₃H₇(n) | |
| 3.15 | cyclopropyl | —CH₃ | |
| 3.16 | cyclopropyl | —C₂H₅ | m.p. 138–139° C. |
| 3.17 | cyclopropyl | —C₃H₇(n) | |
| 3.18 | —C₃H₇(n) | —CH₃ | |
| 3.19 | —C₃H₇(n) | —C₂H₅ | |
| 3.20 | —C₃H₇(n) | —C₃H₇(n) | |
| 3.21 | —C₄H₉(n) | —CH₃ | |
| 3.22 | —C₄H₉(n) | —C₂H₅ | |
| 3.23 | —C₄H₉(n) | —C₃H₇(n) | |
| 3.24 | —CH(CH₃)₂ | —CH₃ | |
| 3.25 | —CH(CH₃)₂ | —C₂H₅ | |
| 3.26 | —CH(CH₃)₂ | —C₃H₇(n) | |
| 3.27 | —CH₂—C₆H₅ | —CH₃ | m.p. 109–111° C. |
| 3.28 | —CH₂—C₆H₅ | —C₂H₅ | |
| 3.29 | —CH₂—C₆H₅ | —C₃H₇(n) | |
| 3.30 | —CH₂—C₆H₄—Cl | —C₃H₇(n) | |
| 3.31 | —CH₂-pyridyl | —C₃H₇(n) | |
| 3.32 | —CH₂-(2-Cl-pyridyl) | —CH₃ | m.p. 165–167° C. |
| 3.33 | —CH₂-(2-Cl-pyridyl) | —C₂H₅ | |

TABLE I-continued

| Compd. No. | $R_2$ | $R_3$ | Physical data |
|---|---|---|---|
| 3.34 | 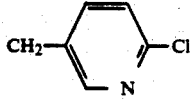 | $-C_3H_7(n)$ | |
| 3.35 | $-CH_3$ | $-CH(CH_3)_2$ | m.p. 154–155° C. |
| 3.36 | $-CH_3$ |  | m.p. 177–178° C. |
| 3.37 | $-CH_3$ | 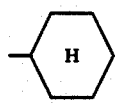 | m.p. 103–104° C. |
| 3.38 | $-CH_3$ | 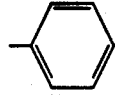 | m.p. 169–172° C. |
| 3.39 | $-CH_3$ | 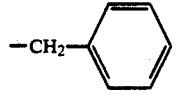 | m.p. 161–163° C. |
| 3.40 | $-CH_3$ | $-CH_2COOCH_3$ | amorphous material |
| 3.41 | $-CH_3$ | $-CH_2CF_3$ | |
| 3.42 | $-CH_3$ | $-CH_2CH_2Br$ | |
| 3.43 | $-CH_3$ | $-CH_2CH_2CH_2Cl$ | |
| 3.44 | $-CH_3$ | $-CH_2CH_2CH_2Br$ | |
| 3.45 | $-CH_3$ | $-CH_2CH_2Cl$ | |
| 3.46 | $-CH_3$ | $-CH_2CH(Cl)CH_2CH_2Cl$ | |
| 3.47 | $-CH_3$ | $-CH_2CH_2OH$ | m.p. 121–123° C. |
| 3.48 | $-CH_3$ | $-CH_2CH_2CH_2OH$ | |
| 3.49 | $-CH_3$ | $-CH_2CH_2CH_2CH_2OH$ | m.p. 81–83° C. |
| 3.50 | $-CH_3$ | $-CH_2CH_2CH_2CH_2CH_2OH$ | |
| 3.51 | $-CH_3$ | $-CH(CH_3)CH_2OH$ | amorphous material |
| 3.52 | $-CH_3$ | $-CH(C_2H_5)CH_2OH$ | |
| 3.53 | $-CH_3$ | $-CH_2CH(CH_3)OH$ | |
| 3.54 | $-CH_3$ | $-CH_2CH(OH)CH_2OH$ | |
| 3.55 | $-CH_3$ | $-CH(CH_2OH)_2$ | |
| 3.56 | $-CH_3$ | $-CH_2CH_2OCH_3$ | |
| 3.57 | $-CH_3$ | $-CH_2CH_2CH_2OC_2H_5$ | |
| 3.58 | $-CH_3$ | $-CH(CH_3)CH_2OCH_3$ | |
| 3.59 | $-CH_3$ | $-CH_2CH(OCH_3)_2$ | |
| 3.60 | $-CH_3$ | $-CH_2CH(OC_2H_5)_2$ | |
| 3.61 | $-CH_3$ | $-CH_2CH_2N(CH_3)_2$ | |
| 3.62 | $-CH_3$ | $-CH_2CH_2N(C_2H_5)_2$ | |
| 3.63 | $-CH_3$ | $-CH_2CH_2CH_2N(CH_3)_2$ | |
| 3.64 | $-CH_3$ | $-CH_2CH_2CH_2N(C_2H_5)_2$ | |
| 3.65 | $-CH_3$ | $-CH_2COOC_2H_5$ | |
| 3.66 | $-CH_3$ | $-CH_2CH_2COOC_2H_5$ | m.p. 110–112° C. |
| 3.67 | $-CH_3$ | $-CH(CH_3)CH_2COOC_2H_5$ | |
| 3.68 | $-CH_3$ | $-CH(CH_2OH)COOCH_3$ | |
| 3.69 | $-CH_3$ |  | |
| 3.70 | $-CH_3$ | 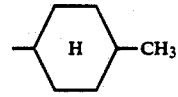 | |
| 3.71 | $-CH_3$ | 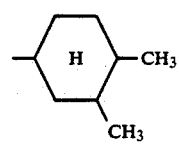 | m.p. 151–153° C. (cis-isomer) m.p. 138–140° C. (trans-isomer) |

TABLE I-continued

| Compd. No. | R$_2$ | R$_3$ | Physical data |
|---|---|---|---|
| 3.72 | —CH$_3$ | 2-methylcyclohexyl | |
| 3.73 | —CH$_3$ | —CH$_2$—CH=CH$_2$ | m.p. 53–55° C. |
| 3.74 | —CH$_3$ | 4-chlorophenyl | |
| 3.75 | —CH$_3$ | 4-fluorophenyl | m.p. 170–173° C. |
| 3.76 | —CH$_3$ | 4-methoxyphenyl | m.p. 174–175° C. |
| 3.77 | —CH$_3$ | 4-methylphenyl | m.p. 195–197° C. |
| 3.78 | —CH$_3$ | 4-nitrophenyl | m.p. 230° C. |
| 3.79 | —CH$_3$ | 4-cyanophenyl | m.p. 222–226° C. |
| 3.80 | —CH$_3$ | 4-trifluoromethylphenyl | m.p. 163–166° C. |
| 3.81 | —CH$_3$ | 2-nitrophenyl | |
| 3.82 | —CH$_3$ | 3-methylthiophenyl | |
| 3.83 | —CH$_3$ | 2-chlorophenyl | |
| 3.84 | —CH$_3$ | 2-cyanophenyl | |

TABLE I-continued

| Compd. No. | R₂ | R₃ | Physical data |
|---|---|---|---|
| 3.85 | —CH₃ | —CH₂—C₆H₄—NO₂ (para) | m.p. 235–238° C. |
| 3.86 | —CH₃ | —CH₂—C₆H₄—F (para) | m.p. 143–145° C. |
| 3.87 | —CH₃ | —CH₂—C₆H₄—OCH₃ (para) | m.p. 132–134° C. |
| 3.88 | —CH₃ | —CH₂—C₆H₄—Cl (para) | m.p. 160–162° C. |
| 3.89 | —CH₃ | —CH₂—C₆H₄—CH₃ (para) | m.p. 161–163° C. |
| 3.90 | —CH₃ | —CH₂—C₆H₄—CF₃ (para) | |
| 3.91 | —CH₃ | —CH₂—C₆H₄—NO₂ (meta) | |
| 3.92 | —CH₃ | —CH₂—C₆H₄—F (ortho) | |
| 3.93 | —CH₃ | —CH₂—C₆H₃—F,F (2,4) | |
| 3.94 | —CH₃ | —CH₂—C₆H₄—CN (meta) | |

EXAMPLE 2

Preparation of the starting compounds of the formula II a) Preparation of 1-(2-chloropyrid-5-ylmethyl)-2-nitroimino-5-cyclopropyl-1,3,5-triazacyclohexane:

A mixture of 2.96 g of 2-nitroimino-5-cyclopropyl-1,3,5-triazacyclohexane, 2.59 g of 2-chloro-5-chloromethylpyridine and 2.43 g of potassium carbonate in 60 ml of acetonitrile is heated under reflux for 16 hours. The reaction mixture obtained is filtered, the filtrate is evaporated in vacuo and the residue formed is chromatographed on silica gel using dichloromethane/ethyl acetate (1:1). 1.73 g of the title compound, m.p. 125°–127° C., of the formula

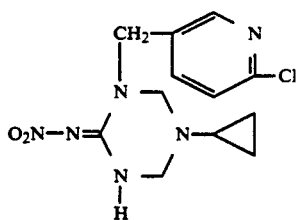

(Compound No. 2.05)

are obtained.

b) Preparation of 1-(2-chloropyrid-5-ylmethyl)-2-nitroimino-3-methyl-5-n-propyl-1,3,5-triazacyclohexane:

A mixture of 20.1 g of 1-methyl-2-nitroimino-5-n-propyl-1,3,5-triazacyclohexane, 16.2 g of 2-chloro-5-chloromethylpyridine, 0.17 g of caesium chloride and 27.7 g of potassium carbonate in 150 ml of dimethylformamide is heated at 110° C. for 9 hours and then filtered through celite. The filtrate is evaporated in vacuo. The crude product obtained is dissolved in 200 ml of dichloromethane and the solution is washed with 100 ml of water and 100 ml of saturated NaCl solution, dried over MgSO₄ and then evaporated. The residue is recrystallised from ethyl acetate. 17.4 g of the title compound, m.p.: 137°–138° C., of the formula

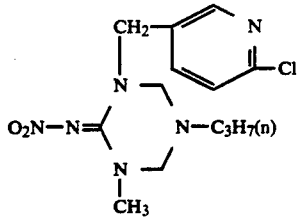

(Compound No. 2.11)

are thus obtained.

The following compounds of the formula II shown in Table II are prepared analogously to the working methods described above:

TABLE II

| Compd. No. | A | R₁ | R₂ | R₃ | Physical data |
|---|---|---|---|---|---|
| 2.01 | Cl-pyridyl | H | H | —CH₃ | m.p. 157–159° C. |
| 2.02 | Cl-pyridyl | H | H | —C₂H₅ | m.p. 125–126° C. |
| 2.03 | Cl-pyridyl | H | H | —C₃H₇(n) | m.p. 115–117° C. |
| 2.04 | Cl-pyridyl | H | H | —CH(CH₃)₂ | m.p. 99–100° C. |
| 2.05 | Cl-pyridyl | H | H | cyclopropyl | m.p. 125–127° C. |
| 2.06 | Cl-pyridyl | H | H | cyclohexyl | m.p. 150–151° C. |
| 2.07 | Cl-pyridyl | H | H | phenyl | m.p. 143–145° C. |
| 2.08 | Cl-pyridyl | H | H | —CH₂—phenyl | m.p. 108–110° C. |

TABLE II-continued

| Compd. No. | A | $R_1$ | $R_2$ | $R_3$ | Physical data |
|---|---|---|---|---|---|
| 2.09 | 6-chloropyridin-3-yl | H | —CH$_3$ | —CH$_3$ | amorphous material |
| 2.10 | 6-chloropyridin-3-yl | H | —CH$_3$ | —C$_2$H$_5$ | m.p. 124–125° C. |
| 2.11 | 6-chloropyridin-3-yl | H | —CH$_3$ | —C$_3$H$_7$(n) | m.p. 137–138° C. |
| 2.12 | 6-chloropyridin-3-yl | H | —C$_2$H$_5$ | —CH$_3$ | |
| 2.13 | 6-chloropyridin-3-yl | H | —C$_2$H$_5$ | —C$_2$H$_5$ | m.p. 113–114° C. |
| 2.14 | 6-chloropyridin-3-yl | H | —C$_2$H$_5$ | —C$_3$H$_7$(n) | |
| 2.15 | 6-chloropyridin-3-yl | H | —C$_3$H$_7$(n) | —CH$_3$ | |
| 2.16 | 6-chloropyridin-3-yl | H | —C$_3$H$_7$(n) | —C$_2$H$_5$ | |
| 2.17 | 6-chloropyridin-3-yl | H | —C$_3$H$_7$(n) | —C$_3$H$_7$(n) | m.p. 112–113° C. |
| 2.18 | 6-chloropyridin-3-yl | H | —CH(CH$_3$)$_2$ | —C$_3$H$_7$(n) | |
| 2.19 | 6-chloropyridin-3-yl | H | cyclopropyl | —CH$_3$ | |
| 2.20 | 6-chloropyridin-3-yl | H | cyclopropyl | —C$_2$H$_5$ | m.p. 115–116° C. |
| 2.21 | 6-chloropyridin-3-yl | H | cyclopropyl | —C$_3$H$_7$(n) | |

TABLE II-continued

| Compd. No. | A | $R_1$ | $R_2$ | $R_3$ | Physical data |
|---|---|---|---|---|---|
| 2.22 | 6-chloro-pyridin-3-yl | H | $-C_4H_9(n)$ | $-C_3H_7(n)$ | |
| 2.23 | 6-chloro-pyridin-3-yl | H | $-CH_2-C_6H_5$ | $-C_3H_7(n)$ | m.p. 127–129° C. |
| 2.24 | 6-chloro-pyridin-3-yl | H | $-CH_2-C_6H_4-Cl$ | $-C_3H_7(n)$ | |
| 2.25 | 6-chloro-pyridin-3-yl | H | $-CH_2-$pyridin-3-yl | $-C_3H_7(n)$ | |
| 2.26 | 6-chloro-pyridin-3-yl | H | $-CH_2-$(6-chloro-pyridin-3-yl) | $-C_3H_7(n)$ | |
| 2.27 | 6-chloro-pyridin-3-yl | $-CH_3$ | $-CH_3$ | $-C_3H_7(n)$ | |
| 2.28 | 6-chloro-pyridin-3-yl | $-CH_3$ | $-C_2H_5$ | $-C_3H_7(n)$ | |
| 2.29 | 6-chloro-pyridin-3-yl | $-CH_3$ | cyclopropyl | $-C_3H_7(n)$ | |
| 2.30 | 6-chloro-pyridin-3-yl | $-C_2H_5$ | $-CH_3$ | $-C_3H_7(n)$ | |
| 2.31 | 6-chloro-pyridin-3-yl | $-C_2H_5$ | $-C_2H_5$ | $-C_3H_7(n)$ | |
| 2.32 | cyclopropyl | $-C_2H_5$ | cyclopropyl | $-C_3H_7(n)$ | |
| 2.33 | 5,6-dichloro-pyridin-3-yl | $-CH_3$ | $-CH_3$ | $-C_3H_7(n)$ | |
| 2.34 | 5,6-dichloro-pyridin-3-yl | $-CH_3$ | $-C_2H_5$ | $-C_3H_7(n)$ | |

TABLE II-continued

| Compd. No. | A | $R_1$ | $R_2$ | $R_3$ | Physical data |
|---|---|---|---|---|---|
| 2.35 | 2,3-dichloro-5-pyridyl | —CH₃ | cyclopropyl | —C₃H₇(n) | |
| 2.36 | 2,3-dichloro-5-pyridyl | —C₂H₅ | —CH₃ | —C₃H₇(n) | |
| 2.37 | 2,3-dichloro-5-pyridyl | H | H | —C₃H₇(n) | |
| 2.38 | 2,3-dichloro-5-pyridyl | H | —CH₃ | —C₃H₇(n) | |
| 2.39 | 2,3-dichloro-5-pyridyl | H | —C₂H₅ | —C₃H₇(n) | |
| 2.40 | 2,3-dichloro-5-pyridyl | H | cyclopropyl | —C₃H₇(n) | |
| 2.41 | 2,3-dichloro-5-pyridyl | H | —C₃H₇(n) | —C₃H₇(n) | |
| 2.42 | 2,3-dichloro-5-pyridyl | H | —C₄H₉(n) | —C₃H₇(n) | |
| 2.43 | 2-chloro-4-methylthiazol-5-yl | H | H | —CH₃ | m.p. 168–170° C. |
| 2.44 | 2-chloro-4-methylthiazol-5-yl | H | —CH₃ | —CH₃ | |
| 2.45 | 2-chloro-4-methylthiazol-5-yl | H | —CH₃ | —C₃H₇(n) | amorphous material |
| 2.46 | 2-chloro-4-methylthiazol-5-yl | H | —C₂H₅ | —C₃H₇(n) | |
| 2.47 | 2-chloro-4-methylthiazol-5-yl | H | cyclopropyl | —C₃H₇(n) | |

TABLE II-continued

| Compd. No. | A | $R_1$ | $R_2$ | $R_3$ | Physical data |
|---|---|---|---|---|---|
| 2.48 | N=C(Cl)-S-C(CH₃)= (chlorothiazoline) | —CH₃ | —CH₃ | —C₃H₇(n) | |
| 2.49 | N=C(Cl)-S-C(CH₃)= | —CH₃ | cyclopropyl | —C₃H₇(n) | |
| 2.50 | N=C(Cl)-S-C(CH₃)= | —C₂H₅ | —CH₃ | —C₃H₇(n) | |
| 2.51 | N=C(Cl)-S-C(CH₃)= | —CH₃ | —C₂H₅ | —C₃H₇(n) | |
| 2.52 | pyridine N-oxide | H | H | —C₃H₇(n) | |
| 2.53 | pyridine N-oxide | H | —CH₃ | —CH₃ | |
| 2.54 | pyridine N-oxide | H | —CH₃ | —C₃H₇(n) | amorphous material |
| 2.55 | pyridine N-oxide | H | cyclopropyl | —C₃H₇(n) | |
| 2.56 | pyridine N-oxide | H | —C₂H₅ | —C₃H₇(n) | |
| 2.57 | pyridine N-oxide | —CH₃ | —CH₃ | —C₃H₇(n) | |
| 2.58 | pyridine N-oxide | —C₂H₅ | —CH₃ | —C₃H₇(n) | |

TABLE II-continued

| Compd. No. | A | $R_1$ | $R_2$ | $R_3$ | Physical data |
|---|---|---|---|---|---|
| 2.59 | 3-pyridyl N-oxide | —CH$_3$ | cyclopropyl | —C$_3$H$_7$(n) | |
| 2.60 | 3-pyridyl N-oxide | —CH$_3$ | —C$_2$H$_5$ | —C$_3$H$_7$(n) | |
| 2.61 | 2-chloro-5-pyridyl N-oxide | H | H | —C$_3$H$_7$(n) | |
| 2.62 | 2-chloro-5-pyridyl N-oxide | H | —CH$_3$ | —C$_3$H$_7$(n) | m.p. 117–121° C. |
| 2.63 | 2-chloro-5-pyridyl N-oxide | H | —CH$_3$ | —CH$_3$ | |
| 2.64 | 2-chloro-5-pyridyl N-oxide | H | —C$_2$H$_5$ | —C$_3$H$_7$(n) | |
| 2.65 | 2-chloro-5-pyridyl N-oxide | H | cyclopropyl | —C$_3$H$_7$(n) | |
| 2.66 | 2-chloro-5-pyridyl N-oxide | —CH$_3$ | —CH$_3$ | —C$_3$H$_7$(n) | |

TABLE II-continued
| Compd. No. | A | $R_1$ | $R_2$ | $R_3$ | Physical data |
|---|---|---|---|---|---|
| 2.67 | 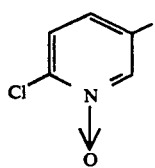 | —$C_2H_5$ | —$CH_3$ | —$C_3H_7(n)$ | |
| 2.68 | 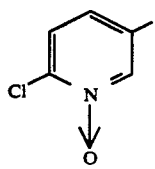 | —$CH_3$ | —$C_2H_5$ | —$C_3H_7(n)$ | |
| 2.69 | 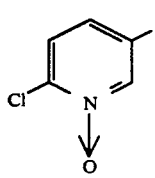 | —$CH_3$ | 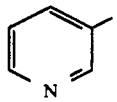 | —$C_3H_7(n)$ | |
| 2.70 | 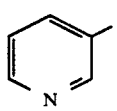 | H | H | —$C_3H_7(n)$ | m.p. 106–108° C. |
| 2.71 | 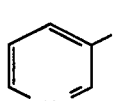 | H | —$CH_3$ | —$C_3H_7(n)$ | |
| 2.72 | 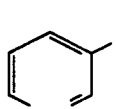 | H | —$C_2H_5$ | —$C_3H_7(n)$ | |
| 2.73 | 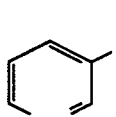 | H | 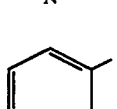 | —$C_3H_7(n)$ | |
| 2.74 | 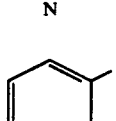 | —$CH_3$ | —$CH_3$ | —$C_3H_7(n)$ | |
| 2.75 | 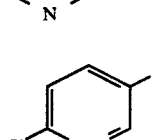 | —$C_2H_5$ | —$CH_3$ | —$C_3H_7(n)$ | |
| 2.76 | | —$CH_3$ | | —$C_3H_7(n)$ | |
| 2.77 | | H | —$CH_3$ | | m.p. 104–106° C. |

TABLE II-continued

| Compd. No. | A | R₁ | R₂ | R₃ | Physical data |
|---|---|---|---|---|---|
| 2.78 | 6-chloro-3-methylpyridin-2-yl | H | —CH₃ | cyclohexyl | m.p. 146–147° C. |
| 2.79 | 6-chloro-3-methylpyridin-2-yl | H | —CH₃ | phenyl | m.p. 146–149° C. |
| 2.80 | 2-chloro-5-methylthiazol-4-yl | H | —CH₃ | —CH₂-phenyl | m.p. 116–118° C. |
| 2.81 | 2-chloro-5-methylthiazol-4-yl | H | —CH₃ | CH₂CH₃ | |
| 2.82 | 2-chloro-5-methylthiazol-4-yl | H | —CH₃ | cyclopropyl | |
| 2.83 | 2-chloro-5-methylthiazol-4-yl | H | —CH₃ | cyclohexyl | |
| 2.84 | 2-chloro-5-methylthiazol-4-yl | H | —CH₃ | phenyl | |
| 2.85 | 2-chloro-5-methylthiazol-4-yl | H | —CH₃ | —CH₂-phenyl | |
| 2.86 | 6-chloro-3-methylpyridin-2-yl | H | —CH₃ | —CH₂COOCH₃ | m.p. 185° C. |
| 2.87 | 2-chloro-5-methylthiazol-4-yl | H | —CH₃ | —CH₂COOCH₃ | |
| 2.88 | 6-chloro-3-methylpyridin-2-yl | H | —CH₃ | —CH₂CF₃ | |
| 2.89 | 2-chloro-5-methylthiazol-4-yl | H | —CH₃ | —CH₂CF₃ | |
| 2.90 | 6-chloro-3-methylpyridin-2-yl | H | —CH₃ | —CH₂CH₂F | |

TABLE II-continued

| Compd. No. | A | $R_1$ | $R_2$ | $R_3$ | Physical data |
|---|---|---|---|---|---|
| 2.91 | 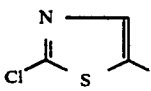 | H | —CH$_3$ | —CH$_2$CH$_2$F | |
| 2.92 | 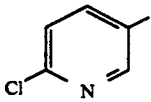 | H | —CH$_3$ | —CH$_2$CH$_2$Br | |
| 2.93 | 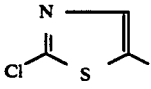 | H | —CH$_3$ | —CH$_2$CH$_2$Br | |
| 2.94 | 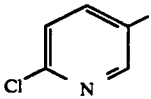 | H | —CH$_3$ | —CH$_2$CH$_2$CH$_2$Cl | |
| 2.95 | 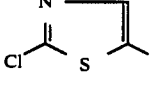 | H | —CH$_3$ | —CH$_2$CH$_2$CH$_2$Cl | |
| 2.96 | 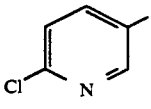 | H | —CH$_3$ | —CH$_2$CH$_2$CH$_2$Br | |
| 2.97 | 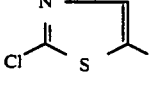 | H | —CH$_3$ | —CH$_2$CH$_2$CH$_2$Br | |
| 2.98 | 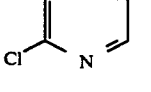 | H | —CH$_3$ | —CH$_2$CH$_2$Cl | |
| 2.99 | 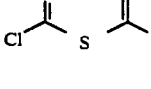 | H | —CH$_3$ | —CH$_2$CH$_2$Cl | |
| 2.100 | 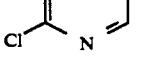 | H | —CH$_3$ | —CH$_2$CH$_2$OH | amorphous material |
| 2.101 | 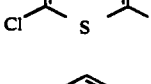 | H | —CH$_3$ | —CH$_2$CH$_2$OH | |
| 2.102 | 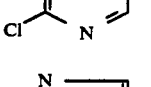 | H | —CH$_3$ | —CH$_2$CH$_2$CH$_2$OH | amorphous material |
| 2.103 | 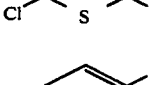 | H | —CH$_3$ | —CH$_2$CH$_2$CH$_2$OH | |
| 2.104 | 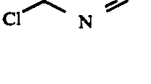 | H | —CH$_3$ | —CH$_2$CH$_2$CH$_2$CH$_2$OH | m.p. 108–110° C. |

TABLE II-continued
| Compd. No. | A | $R_1$ | $R_2$ | $R_3$ | Physical data |
|---|---|---|---|---|---|
| 2.105 | 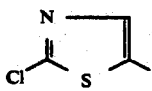 | H | —$CH_3$ | —$CH_2CH_2CH_2CH_2OH$ | |
| 2.106 | 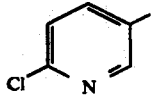 | H | —$CH_3$ | —$CH(CH_3)CH_2OH$ | amorphous material |
| 2.107 | 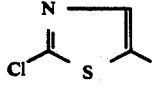 | H | —$CH_3$ | —$CH(CH_3)CH_2OH$ | |
| 2.108 | 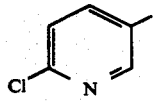 | H | —$CH_3$ | —$CH(C_2H_5)CH_2OH$ | |
| 2.109 | 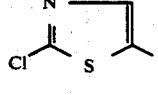 | H | —$CH_3$ | —$CH(C_2H_5)CH_2OH$ | |
| 2.110 | 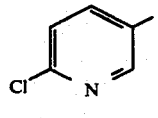 | H | —$CH_3$ | —$CH(CH_2OH)_2$ | |
| 2.111 | 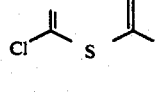 | H | —$CH_3$ | —$CH(CH_2OH)_2$ | |
| 2.112 | 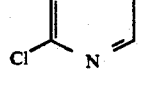 | H | —$CH_3$ | —$CH_2CH_2OCH_3$ | |
| 2.113 | 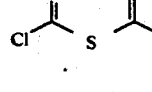 | H | —$CH_3$ | —$CH_2CH_2OCH_3$ | |
| 2.114 | 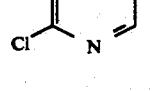 | H | —$CH_3$ | —$CH_2CH_2CH_2OC_2H_5$ | |
| 2.115 | 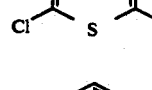 | H | —$CH_3$ | —$CH_2CH_2CH_2OC_2H_5$ | |
| 2.116 | 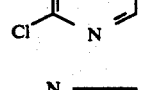 | H | —$CH_3$ | —$CH(CH_3)CH_2OCH_3$ | |
| 2.117 | 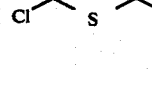 | H | —$CH_3$ | —$CH(CH_3)CH_2OCH_3$ | |

TABLE II-continued

| Compd. No. | A | R₁ | R₂ | R₃ | Physical data |
|---|---|---|---|---|---|
| 2.118 | 6-chloro-3-pyridyl | H | —CH₃ | —CH₂CH(OCH₃)₂ | |
| 2.119 | 2-chloro-5-thiazolyl | H | —CH₃ | —CH₂CH(OCH₃)₂ | |
| 2.120 | 6-chloro-3-pyridyl | H | —CH₃ | —CH₂CH₂N(CH₃)₂ | |
| 2.121 | 2-chloro-5-thiazolyl | H | —CH₃ | —CH₂CH₂N(CH₃)₂ | |
| 2.122 | 6-chloro-3-pyridyl | H | —CH₃ | —CH₂CH₂N(C₂H₅)₂ | |
| 2.123 | 2-chloro-5-thiazolyl | H | —CH₃ | —CH₂CH₂N(C₂H₅)₂ | |
| 2.124 | 6-chloro-3-pyridyl | H | —CH₃ | —CH₂CH₂CH₂N(CH₃)₂ | |
| 2.125 | 2-chloro-5-thiazolyl | H | —CH₃ | —CH₂CH₂CH₂N(CH₃)₂ | |
| 2.126 | 6-chloro-3-pyridyl | H | —CH₃ | —CH₂CH₂COOC₂H₅ | m.p. 78–80° C. |
| 2.127 | 2-chloro-5-thiazolyl | H | —CH₃ | —CH₂CH₂COOC₂H₅ | |
| 2.128 | 6-chloro-3-pyridyl | H | —CH₃ | —CH₂COOC₂H₅ | amorphous material |
| 2.129 | 2-chloro-5-thiazolyl | H | —CH₃ | —CH₂COOC₂H₅ | |
| 2.130 | 6-chloro-3-pyridyl | H | —CH₃ | —CH(CH₃)CH₂COOC₂H₅ | |
| 2.131 | 2-chloro-5-thiazolyl | H | —CH₃ | —CH(CH₃)CH₂COOC₂H₅ | |

TABLE II-continued

| Compd. No. | A | R₁ | R₂ | R₃ | Physical data |
|---|---|---|---|---|---|
| 2.132 | 6-chloro-3-methylpyridin-2-yl | H | —CH₃ | cyclopentyl (H) | |
| 2.133 | 2-chloro-5-methylthiazol-4-yl | H | —CH₃ | cyclopentyl (H) | |
| 2.134 | 6-chloro-3-methylpyridin-2-yl | H | —CH₃ | 4-methylcyclohexyl (H, CH₃) | m.p.137–139° C. (cis-isomers) m.p. 170–172° C. (trans-isomers) |
| 2.135 | 2-chloro-5-methylthiazol-4-yl | H | —CH₃ | 4-methylcyclohexyl (H, CH₃) | |
| 2.136 | 6-chloro-3-methylpyridin-2-yl | H | —CH₃ | —CH₂—CH=CH₂ | m.p. 75–77° C. |
| 2.137 | 2-chloro-5-methylthiazol-4-yl | H | —CH₃ | —CH₂—CH=CH₂ | |
| 2.138 | 6-chloro-3-methylpyridin-2-yl | H | —CH₃ | 4-chlorophenyl | |
| 2.139 | 2-chloro-5-methylthiazol-4-yl | H | —CH₃ | 4-chlorophenyl | |
| 2.140 | 6-chloro-3-methylpyridin-2-yl | H | —CH₃ | 4-fluorophenyl | amorphous material |
| 2.141 | 2-chloro-5-methylthiazol-4-yl | H | —CH₃ | 4-fluorophenyl | |
| 2.142 | 6-chloro-3-methylpyridin-2-yl | H | —CH₃ | 4-methoxyphenyl | m.p. 204° C. |
| 2.143 | 2-chloro-5-methylthiazol-4-yl | H | —CH₃ | 4-methoxyphenyl | |
| 2.144 | 6-chloro-3-methylpyridin-2-yl | H | —CH₃ | 4-methylphenyl | amorphous material |

TABLE II-continued

| Compd. No. | A | $R_1$ | $R_2$ | $R_3$ | Physical data |
|---|---|---|---|---|---|
| 2.145 | 2-chloro-thiazol-5-yl-methyl (N=C(Cl)-S-CH=C(CH₃)-) | H | $-CH_3$ | 4-methylphenyl | |
| 2.146 | 6-chloro-pyridin-3-yl | H | $-CH_3$ | 4-nitrophenyl | m.p. 219° C. |
| 2.147 | 2-chloro-thiazol-5-yl-methyl | H | $-CH_3$ | 4-nitrophenyl | |
| 2.148 | 6-chloro-pyridin-3-yl | H | $-CH_3$ | 4-cyanophenyl | amorphous material |
| 2.149 | 2-chloro-thiazol-5-yl-methyl | H | $-CH_3$ | 4-cyanophenyl | |
| 2.150 | 6-chloro-pyridin-3-yl | H | $-CH_3$ | 4-trifluoromethylphenyl | amorphous material |
| 2.151 | 2-chloro-thiazol-5-yl-methyl | H | $-CH_3$ | 4-trifluoromethylphenyl | |
| 2.152 | 6-chloro-pyridin-3-yl | H | $-CH_3$ | 2-nitrophenyl | |
| 2.153 | 2-chloro-thiazol-5-yl-methyl | H | $-CH_3$ | 2-nitrophenyl | |
| 2.154 | 6-chloro-pyridin-3-yl | H | $-CH_3$ | 3-methylthiophenyl | |
| 2.155 | 2-chloro-thiazol-5-yl-methyl | H | $-CH_3$ | 3-methylthiophenyl | |
| 2.156 | 6-chloro-pyridin-3-yl | H | $-CH_3$ | 2-chlorophenyl | |

TABLE II-continued
| Compd. No. | A | $R_1$ | $R_2$ | $R_3$ | Physical data |
|---|---|---|---|---|---|
| 2.157 | 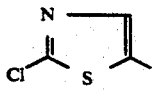 | H | —CH$_3$ | 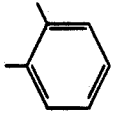 | |
| 2.158 | 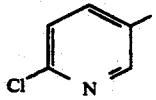 | H | —CH$_3$ | 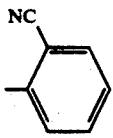 | |
| 2.159 | 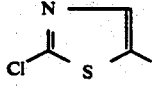 | H | —CH$_3$ | 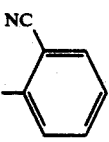 | |
| 2.160 | 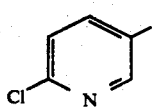 | H | —CH$_3$ | 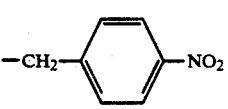 | amorphous material |
| 2.161 | 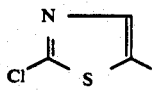 | H | —CH$_3$ | 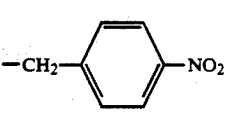 | |
| 2.162 | 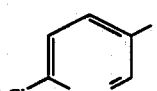 | H | —CH$_3$ | 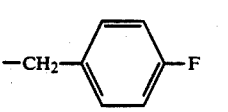 | m.p. 162–164° C. |
| 2.163 | 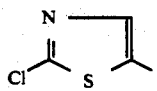 | H | —CH$_3$ | 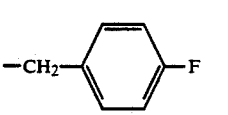 | |
| 2.164 | 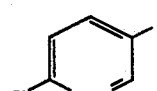 | H | —CH$_3$ | 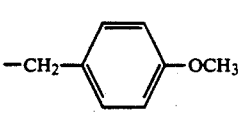 | m.p. 125–127° C. |
| 2.165 | 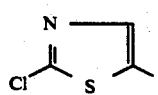 | H | —CH$_3$ | 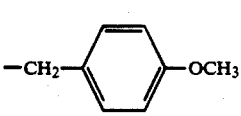 | |
| 2.166 | 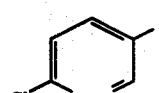 | H | —CH$_3$ | 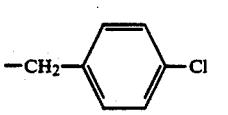 | m.p. 147–149° C. |
| 2.167 | 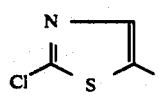 | H | —CH$_3$ | 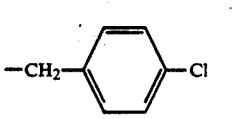 | |
| 2.168 | 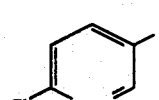 | H | —CH$_3$ | 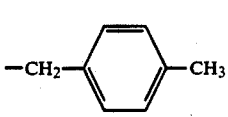 | m.p. 155–157° C. |

TABLE II-continued
| Compd. No. | A | R₁ | R₂ | R₃ | Physical data |
|---|---|---|---|---|---|
| 2.169 | 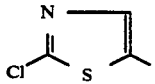 | H | —CH₃ | 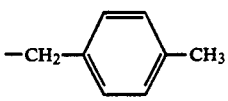 | |
| 2.170 | 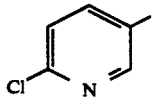 | H | —CH₃ | 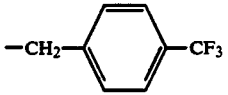 | m.p. 167–169° C. |
| 2.171 | 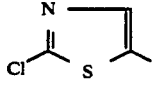 | H | —CH₃ | 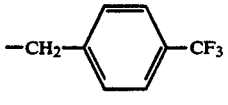 | |
| 2.172 | 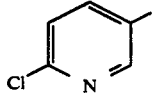 | H | —CH₃ | 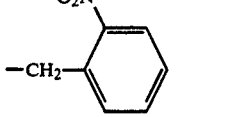 | |
| 2.173 | 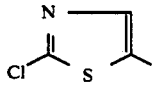 | H | —CH₃ | 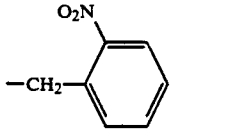 | |
| 2.174 | 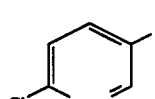 | H | —CH₃ | 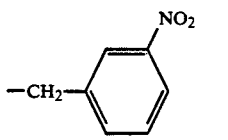 | |
| 2.175 | 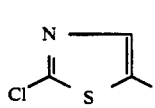 | H | —CH₃ | 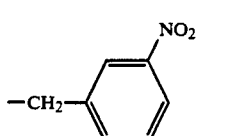 | |
| 2.176 | 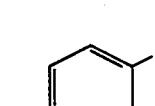 | H | —CH₃ | 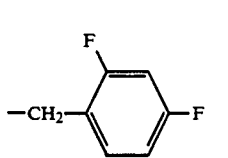 | |
| 2.177 | 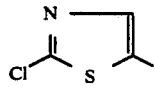 | H | —CH₃ | 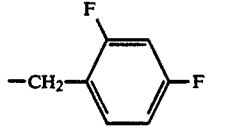 | |
| 2.178 | 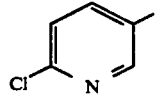 | H | —CH₃ | 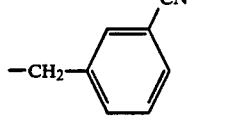 | |
| 2.179 | 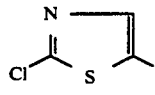 | H | —CH₃ | 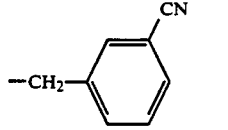 | |

TABLE II-continued

| Compd. No. | A | $R_1$ | $R_2$ | $R_3$ | Physical data |
|---|---|---|---|---|---|
| 2.180 | 6-Cl-pyridin-3-yl N-oxide | H | —CH$_3$ | —CH$_2$CH$_3$ | m.p. 152–155° C. |
| 2.181 | 6-Cl-pyridin-3-yl N-oxide | H | —CH$_3$ | —CH(CH$_3$)$_2$ | m.p. 138° C. |
| 2.182 | 6-Cl-pyridin-3-yl N-oxide | H | —CH$_3$ | cyclohexyl | m.p. 153° C. |
| 2.183 | pyridin-3-yl N-oxide | H | —CH$_3$ | cyclopropyl | m.p. 185° C. |
| 2.184 | pyridin-3-yl | H | H | —CH$_3$ | m.p. 142–144° C. |
| 2.185 | 6-Cl-pyridin-3-yl | H | H | —CH$_2$COOCH$_3$ | m.p. 184–186° C. |
| 2.186 | 5,6-diCl-pyridin-3-yl N-oxide | H | —CH$_3$ | —C$_3$H$_7$-n | m.p. 157–158° C. |
| 2.187 | pyridin-3-yl | H | H | —CH$_2$-phenyl | m.p. 157–159° C. |
| 2.188 | 6-Cl-pyridin-3-yl | H | H | —CH$_2$CH$_2$OCH$_3$ | m.p. 80–82° C. |
| 2.189 | 6-Cl-pyridin-3-yl | H | H | —CH$_2$-(4-Cl-phenyl) | m.p. 162–164° C. |

TABLE II-continued

| Compd. No. | A | R₁ | R₂ | R₃ | Physical data |
|---|---|---|---|---|---|
| 2.190 | 2-chloro-5-pyridyl | H | H | —CH₂CH₂OH | m.p. 142–144° C. |
| 2.191 | 2-chloro-5-pyridyl | H | H | —CH₂CH₂—N(CH₃)₂ | m.p. 104–106° C. |

EXAMPLE 3

Preparation of compounds of the formula I a) Preparation of 1-(2-chloropyrid-5-ylmethyl)-2-nitro-3-n-propylguanidine:

A solution of 1.35 g of 1-(2-chloropyrid-5-ylmethyl)-2-nitroimino-3,5-(di-n-propyl)-1,3,5-triazacyclohexane, 3 ml of acetic acid and 2 ml of water in 10 ml of methanol is heated at 50° C. for 3 days. The mixture is then poured onto 100 ml of ethyl acetate and washed successively with 50 ml portions of saturated NaCl, saturated NaHCO₃ and saturated NaCl solution. The separated organic phase is dried over MgSO₄ and evaporated. The crude product obtained as residue is chromatographed on silica gel using hexane/ethyl acetate (1:2). 0.80 g of the title compound, m.p. 120°–123° C. of the formula

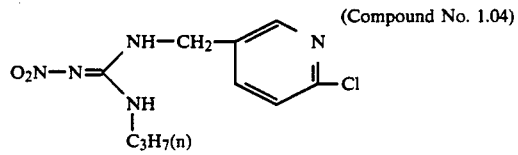

(Compound No. 1.04)

is thus obtained.

b) Preparation of 1-(2-chloropyrid-5-ylmethyl)-2-nitro-3-methylguanidine:

A solution of 4.25 g of 1-(2-chloropyrid-5-ylmethyl)-2-nitroimino-3-methyl-5-n-propyl-1,3,5-triazacyclohexane in 26 ml of methanol is treated with 26 ml of 1N HCl and stirred at room temperature for 16 hours. The reaction mixture is filtered, and the crystals removed by filtration are washed with a little methanol and dried. 2.51 g of the title compound, m.p. 148°–150° C., of the formula

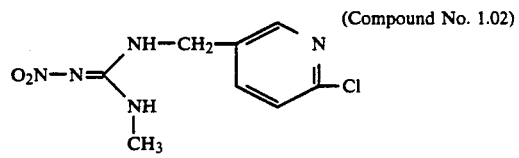

(Compound No. 1.02)

are thus obtained.

The following compounds of the formula I shown in Table III can also be obtained analogously to the above working methods:

TABLE III

| Compd. No. | A | R₁ | R₂ | Physical data |
|---|---|---|---|---|
| 1.01 | 2-chloro-5-pyridyl | H | H | m.p. 195–197° C. |
| 1.02 | 2-chloro-5-pyridyl | H | —CH₃ | m.p. 148–150° C. |
| 1.03 | 2-chloro-5-pyridyl | H | —C₂H₅ | m.p. 125–127° C. |
| 1.04 | 2-chloro-5-pyridyl | H | —C₃H₇(n) | m.p. 122–123° C. |
| 1.05 | 2-chloro-5-pyridyl | H | cyclopropyl | |

TABLE III-continued
| Compd. No. | A | R₁ | R₂ | Physical data |
|---|---|---|---|---|
| 1.06 | 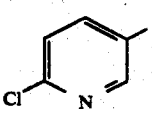 | H | —C₄H₉(n) | m.p. 88–90° C. |
| 1.07 | 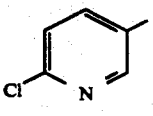 | H | —CH(CH₃)₂ | |
| 1.08 | 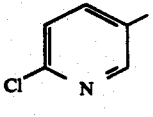 | H | —CH₂—C₆H₅ | |
| 1.09 | 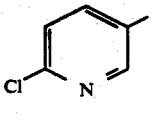 | H | —CH₂-pyridyl | |
| 1.10 | 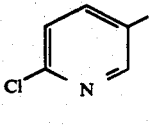 | H | —CH₂-(6-Cl-pyridyl) | |
| 1.11 | 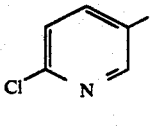 | H | —CH₂—C₆H₄—Cl | |
| 1.12 | 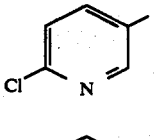 | —CH₃ | —CH₃ | |
| 1.13 | 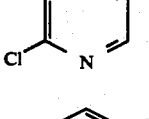 | —CH₃ | —C₂H₅ | |
| 1.14 | 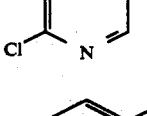 | —CH₃ |  | |
| 1.15 | 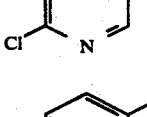 | —CH₃ | —C₃H₇(n) | |
| 1.16 | 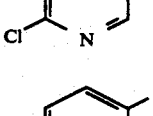 | —C₂H₅ | —CH₃ | |
| 1.17 | 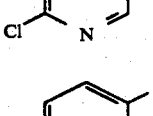 | —C₂H₅ | —C₂H₅ | |
| 1.18 | 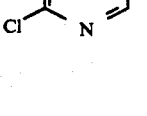 | —C₂H₅ |  | |

TABLE III-continued

| Compd. No. | A | $R_1$ | $R_2$ | Physical data |
|---|---|---|---|---|
| 1.19 | 3-pyridyl | H | H | m.p. 201–202° C. |
| 1.20 | 3-pyridyl | H | —CH₃ | m.p. 162–163° C. |
| 1.21 | 3-pyridyl | H | —C₂H₅ | m.p. 113–116° C. |
| 1.22 | 3-pyridyl | —CH₃ | H | m.p. 158–160° C. |
| 1.23 | 3-pyridyl | —CH₃ | —CH₃ | m.p. 161–163° C. |
| 1.24 | 3-pyridyl | —CH₃ | cyclopropyl | |
| 1.25 | 3-pyridyl | H | cyclopropyl | |
| 1.26 | 2,3-dichloro-5-pyridyl | H | H | m.p. 207–209° C. |
| 1.27 | 2,3-dichloro-5-pyridyl | H | —CH₃ | m.p. 173–175° C. |
| 1.28 | 2,3-dichloro-5-pyridyl | H | —C₂H₅ | m.p. 159–161° C. |
| 1.29 | 2,3-dichloro-5-pyridyl | H | cyclopropyl | |
| 1.30 | 2,3-dichloro-5-pyridyl | H | —C₃H₇(n) | |

TABLE III-continued

| Compd. No. | A | R₁ | R₂ | Physical data |
|---|---|---|---|---|
| 1.31 | 2,3-dichloropyridin-5-yl | H | —C₄H₉(n) | m.p. 152–153° C. |
| 1.32 | 2,3-dichloropyridin-5-yl | —CH₃ | —CH₃ | |
| 1.33 | 2,3-dichloropyridin-5-yl | —CH₃ | —C₂H₅ | |
| 1.34 | 2,3-dichloropyridin-5-yl | —CH₃ | cyclopropyl | |
| 1.35 | 2,3-dichloropyridin-5-yl | —C₂H₅ | —CH₃ | |
| 1.36 | pyridin-3-yl N-oxide | H | H | |
| 1.37 | pyridin-3-yl N-oxide | H | —CH₃ | |
| 1.38 | pyridin-3-yl N-oxide | H | —C₂H₅ | |
| 1.39 | pyridin-3-yl N-oxide | H | cyclopropyl | |
| 1.40 | pyridin-3-yl N-oxide | —CH₃ | —CH₃ | |

TABLE III-continued

| Compd. No. | A | R₁ | R₂ | Physical data |
|---|---|---|---|---|
| 1.41 | 3-methylpyridine N-oxide | —CH₃ | —C₂H₅ | |
| 1.42 | 3-methylpyridine N-oxide | —CH₃ | cyclopropyl | |
| 1.43 | 3-methylpyridine N-oxide | —C₂H₅ | —CH₃ | |
| 1.44 | 2-chloro-5-pyridine N-oxide | H | H | |
| 1.45 | 2-chloro-5-pyridine N-oxide | H | —CH₃ | |
| 1.46 | 2-chloro-5-pyridine N-oxide | H | —C₂H₅ | |
| 1.47 | 2-chloro-5-pyridine N-oxide | H | cyclopropyl | |
| 1.48 | 2-chloro-5-pyridine N-oxide | —CH₃ | —CH₃ | |

TABLE III-continued

| Compd. No. | A | $R_1$ | $R_2$ | Physical data |
|---|---|---|---|---|
| 1.49 | 2-Cl-pyridin-5-yl N-oxide | —CH$_3$ | cyclopropyl | |
| 1.50 | 2-Cl-pyridin-5-yl N-oxide | —CH$_3$ | —C$_2$H$_5$ | |
| 1.51 | 2-Cl-pyridin-5-yl N-oxide | —C$_2$H$_5$ | —CH$_3$ | |
| 1.52 | 2-Cl-thiazol-5-yl | H | H | m.p. 158–160° C. |
| 1.53 | 2-Cl-thiazol-5-yl | H | —CH$_3$ | m.p. 168–170° C. |
| 1.54 | 2-Cl-thiazol-5-yl | H | —C$_2$H$_5$ | m.p. 135–136° C. |
| 1.55 | 2-Cl-thiazol-5-yl | H | cyclopropyl | |
| 1.56 | 2-Cl-thiazol-5-yl | H | —CH$_2$—C$_6$H$_5$ | |
| 1.57 | 2-Cl-thiazol-5-yl | H | —CH$_2$—C$_6$H$_4$—Cl | |
| 1.58 | 2-Cl-thiazol-5-yl | —CH$_3$ | —CH$_3$ | |
| 1.59 | 2-Cl-thiazol-5-yl | —C$_2$H$_5$ | —CH$_3$ | |
| 1.60 | 2-Cl-thiazol-5-yl | —CH$_3$ | —C$_2$H$_5$ | |

TABLE III-continued

| Compd. No. | A | $R_1$ | $R_2$ | Physical data |
|---|---|---|---|---|
| 1.61 | 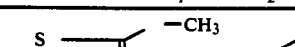 | —CH$_3$ |  | |
| 1.62 | 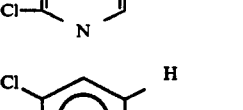 | H | H | |

What is claimed is:

1. A process for the preparation of a compound of the formula I

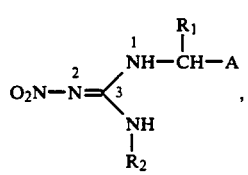

in which $R_1$ is hydrogen or $C_1$-$C_4$alkyl, $R_2$ is hydrogen, $C_1$-$C_6$alkyl, $C_3$-$C_6$cycloalkyl or a radical —CH$_2$B;

A is an unsubstituted or mono- to tetrasubstituted aromatic or non-aromatic, monocyclic or bicyclic heterocyclic radical, which may contain one or two substituents selected from the group consisting of $C_1$-$C_3$haloalkyl having 1 to 7 halogen atoms, cyclopropyl, halocyclopropyl having 1 to 3 halogen atoms, $C_2$-$C_3$alkenyl, $C_2$-$C_3$alkynyl, $C_2$-$C_3$-haloalkenyl and $C_2$-$C_3$haloalkylnyl having 1 to 4 halogen atoms, $C_1$-$C_3$haloalkoxy having 1 to 7 halogen atoms, $C_1$-$C_3$alkylthio, $C_1$-$C_3$haloalkylthio having 1 to 7 halogen atoms, allyloxy, propargyloxy, allylthio, propargylthio, haloallyloxy, haloallylthio, cyano and nitro; and one to four substituents selected from the group consisting of $C_1$-$C_3$alkyl, $C_1$-$C_3$alkoxy and halogen; and B is phenyl, cyanophenyl, nitrophenyl, halophenyl having 1 to 3 halogen atoms, phenyl substituted by $C_1$-$C_3$alkyl, $C_1$-$C_3$haloalkyl having 1 to 7 halogen atoms, $C_1$-$C_3$alkoxy or $C_1$-$C_3$haloalkoxy having 1 to 7 halogen atoms, 3-pyridyl, 5-thiazolyl, 5-thiazolyl substituted by one or two substituents selected from the group consisting of $C_1$-$C_3$alkyl, $C_1$-$C_3$-haloalkyl having 1 to 7 halogen atoms, cyclopropyl, halocyclopropyl, $C_2$-$C_3$alkenyl, $C_2$-$C_3$alkynyl, $C_1$-$C_3$alkoxy, $C_2$-$C_3$haloalkenyl and $C_2$-$C_3$-haloalkynyl having 1 to 4 halogen atoms, $C_1$-$C_3$-haloalkoxy having 1 to 7 halogen atoms, $C_1$-$C_3$alkylthio, $C_1$-$C_3$haloalkylthio having 1 to 7 halogen atoms, allyloxy, propargyloxy, allylthio, propargylthio, haloallyloxy, haloallylthio, halogen, cyano and nitro, or 3-pyridyl substituted by one or two radicals selected from the group consisting of $C_1$-$C_3$haloalkyl having 1 to 7 halogen atoms, cyclopropyl, halocyclopropyl, $C_2$-$C_3$alkenyl, $C_2$-$C_3$alkynyl, $C_2$-$C_3$haloalkenyl and $C_2$-$C_3$haloalkynyl having 1 to 4 halogen atoms, $C_1$-$C_3$haloalkoxy having 1 to 7 halogen atoms, $C_1$-$C_3$alkylthio, $C_1$-$C_3$haloalkylthio having 1 to 7 halogen atoms, allyloxy, propargyloxy, allylthio, propargylthio, haloallyloxy, haloallylthio, cyano and nitro or by one to four radicals selected from the group consisting of $C_1$-$C_3$alkyl, $C_1$-$C_3$alkoxy and halogen, which comprises hydrolyzing a compound of the formula II

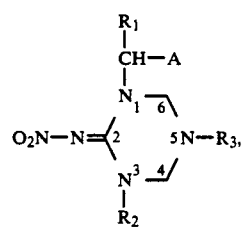

in which $R_3$ is $C_1$-$C_{10}$alkyl, $C_3$-$C_6$cycloalkyl, $C_1$-$C_{10}$alkyl substituted by 1-12 radicals selected from the group consisting of halogen, hydroxyl, $C_1$-$C_4$alkoxy, $C_1$-$C_4$haloalkoxy having 1 to 9 halogen atoms, di-($C_1$-$C_4$alkyl)amino and $C_1$-$C_5$alkoxycarbonyl, $C_3$-$C_6$cycloalkyl substituted by 1-4 $C_1$-$C_4$alkyl radicals or halogen atoms, phenyl or benzyl, or phenyl or benzyl substituted by 1-3 ring substitutents selected from the group consisting of halogen, $C_1$-$C_4$alkyl, $C_1$-$C_4$haloalkyl having 1 to 9 halogen atoms, $C_1$-$C_4$alkoxy, $C_1$-$C_4$haloalkoxy having 1 to 9 halogen atoms, $C_1$-$C_4$alkylthio, nitro and cyano.

2. A process according to claim 1, wherein the compound of the formula II is hydrolysed by acid.

3. A process according to claim 1, wherein a compound of the formula I is prepared in which the heterocyclic radical A is a heterocyclic parent structure bond to the rest of the molecule of the compound of the formula I via a carbon atom, of the group consisting of

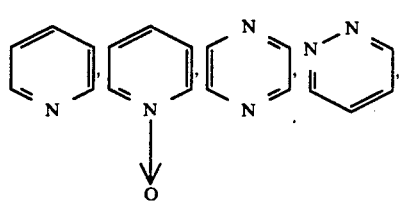

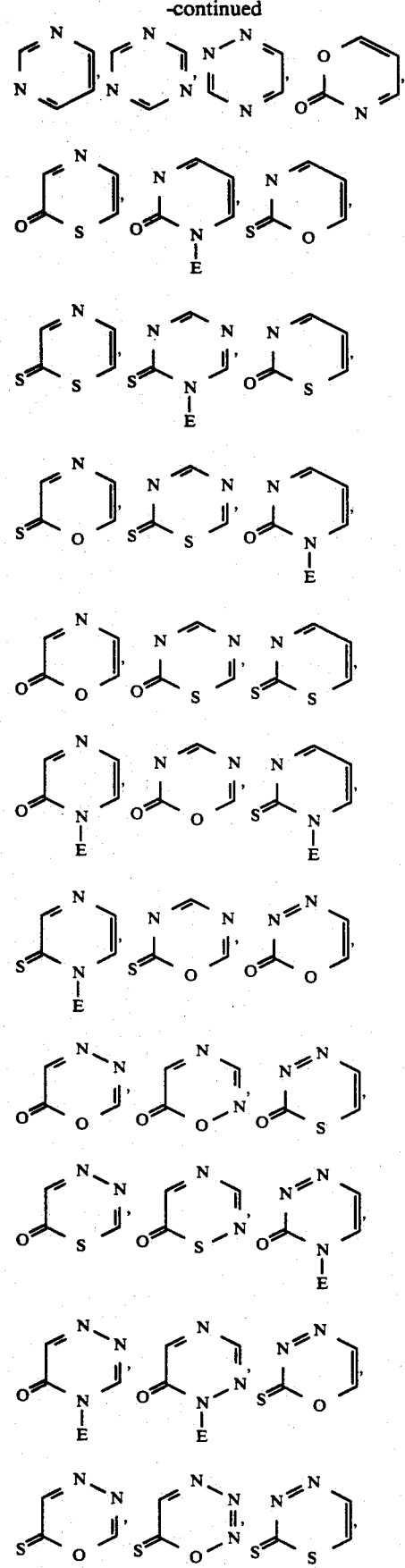
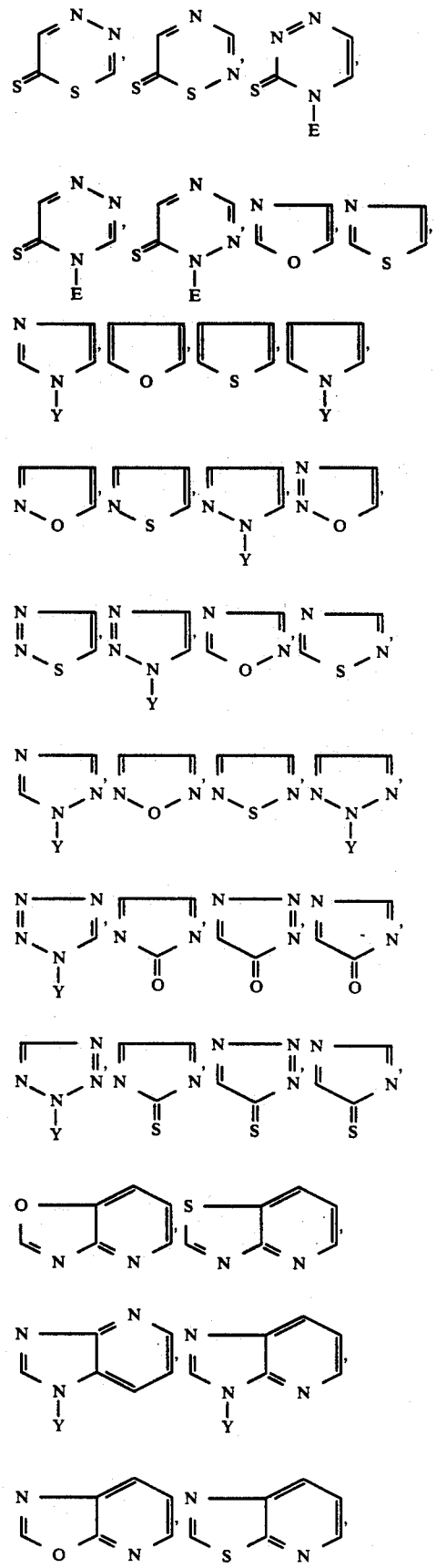

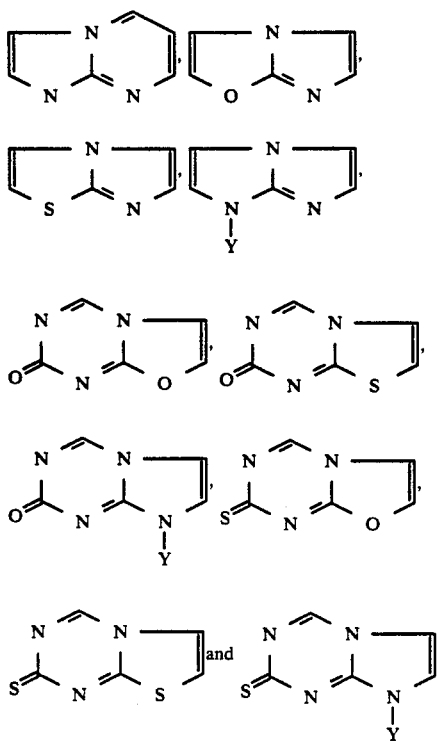

which is unsubstituted or, depending on the substitution possibilities of the ring system, carries up to four of the substituents defined in claim 1 and in which E is $C_1$-$C_3$alkyl and Y is hydrogen, $C_1$-$C_3$alkyl or cyclopropyl.

4. A process according to claim 3, wherein the heterocyclic radical A is unsubstituted or carries one to three substituents from the group consisting of halogen, $C_1$-$C_3$alkyl, $C_1$-$C_3$haloalkyl and $C_1$-$C_3$haloalkoxy having 1 to 7 halogen atoms, and $C_1$-$C_3$alkoxy.

5. A process according to claim 4, wherein A is pyridyl or thiazolyl.

6. A process according to claim 1, wherein the radical B is a phenyl, 3-pyridyl or 5-thiazolyl radical, which is unsubstituted or substituted by one or two radicals from the group consisting of halogen, $C_1$-$C_3$alkyl, $C_1$-$C_3$haloalkyl and $C_1$-$C_3$haloalkoxy having 1 to 7 halogen atoms, and $C_1$-$C_3$alkoxy.

7. A process according to claim 5, wherein the radical A is 3-pyridyl, 2-halopyrid-5-yl, 2,3-dihalopyrid-5-yl or 2-halothiazol-4-yl, 1-oxopyrid-3-yl, 1-oxo-2-halopyrid-5-yl or 1-oxo-2,3-dihalopyrid-5-yl.

8. A process according to claim 1, wherein $R_1$ is hydrogen; $R_2$ is hydrogen, methyl, ethyl or cyclopropyl and A is pyridyl, 1-oxopyridyl, thiazolyl or pyridyl, 1-oxopyridyl or thiazolyl in each case substituted by one to three substituents selected from the group consisting of halogen, $C_1$-$C_3$alkyl, $C_1$-$C_3$haloalkyl and $C_1$-$C_3$haloalkoxy having 1 to 7 halogen atoms, and $C_1$-$C_3$alkoxy.

9. A process according to claim 1, wherein $R_1$ is hydrogen.

10. A process according to claim 1, wherein $R_2$ is hydrogen, $C_1$-$C_3$alkyl or cyclopropyl.

11. A process according to claim 1, wherein A is 2-chloropyrid-5-yl or 2-chlorotriazol-5-yl.

12. A process according to claim 1, wherein $R_2$ is methyl.

13. A process according to claim 1, wherein $R_3$ is $C_1$-$C_3$alkyl, cyclopropyl, cyclohexyl, phenyl or benzyl.

14. A process according to claim 1, wherein A is pyridyl or thiazolyl or substituted pyridyl or thiazolyl.

15. A process according to claim 1, wherein A is pyridyl or substituted pyridyl.

16. A process according to claim 1, wherein A is thiazolyl or substituted thiazolyl.

* * * * *